US012609188B2

(12) United States Patent
Andriopoulou

(10) Patent No.: US 12,609,188 B2
(45) Date of Patent: Apr. 21, 2026

(54) METHOD AND SYSTEM FOR PROVIDING HEALTH RECORD DATA

(71) Applicant: ATOS Public Safety, LLC, Irving, TX (US)

(72) Inventor: Foteini Andriopoulou, Patras (GR)

(73) Assignee: ATOS PUBLIC SAFETY LLC, Irving, TX (US)

( * ) Notice: Subject to any disclaimer, the term of this patent is extended or adjusted under 35 U.S.C. 154(b) by 475 days.

(21) Appl. No.: 18/318,761

(22) Filed: May 17, 2023

(65) Prior Publication Data

US 2024/0145046 A1 May 2, 2024

(30) Foreign Application Priority Data

Oct. 27, 2022 (EP) ..................................... 22204242

(51) Int. Cl.
*G16H 10/60* (2018.01)
*G06V 40/16* (2022.01)
*G16H 50/70* (2018.01)

(52) U.S. Cl.
CPC ........... *G16H 10/60* (2018.01); *G06V 40/172* (2022.01); *G16H 50/70* (2018.01)

(58) Field of Classification Search
CPC ....... G16H 10/60; G16H 50/70; G06V 40/172
See application file for complete search history.

(56) References Cited

U.S. PATENT DOCUMENTS

| | | | | |
|---|---|---|---|---|
| 9,928,379 B1 * | 3/2018 | Hoffer | .................... | G16H 50/20 |
| 10,255,419 B1 * | 4/2019 | Kragh | .................... | H04L 9/321 |
| 10,375,558 B2 * | 8/2019 | Katz | ....................... | H04W 4/90 |
| 11,501,861 B2 * | 11/2022 | Finkelstein | ............ | G16H 10/60 |
| 2014/0207686 A1 | 7/2014 | Experton | | |
| 2017/0068785 A1 | 3/2017 | Experton et al. | | |
| 2019/0035492 A1 | 1/2019 | Finkelstein et al. | | |
| 2020/0118657 A1 | 4/2020 | Finkelstein et al. | | |
| 2020/0346751 A1 | 11/2020 | Horelik et al. | | |

FOREIGN PATENT DOCUMENTS

WO 2016200416 A1 12/2016

OTHER PUBLICATIONS

Extended European Search Report for European Application No. 22204242.6 dated Apr. 13, 2023.

* cited by examiner

*Primary Examiner* — Michael I Ezewoko
(74) *Attorney, Agent, or Firm* — Meagher, Emanuel Laks, Goldberg & Liao, LLP

(57) ABSTRACT

A method for providing health record data includes receiving data from a user, generating a victim dataset from the data, and storing the victim dataset in a victim identification database. The method can also include retrieving from a private database at least one set of private information based on the victim dataset wherein the at least one set of private information matches the victim dataset with a predefinable probability. For each set of the at least one set of private information, activity information from a list of activity databases can be collected. At least one set of aggregated information can be generated that can include private information and activity information associated with the at least one set of private information. At least one set of aggregated information can be selected that best matches the victim dataset for data retrieval.

11 Claims, 4 Drawing Sheets

METHOD AND SYSTEM FOR PROVIDING HEALTH RECORD DATA

CROSS-REFERENCE TO RELATED APPLICATIONS

This application claims priority to European Patent Application No. EP 22 204 242.6 filed on Oct. 27, 2022. The entirety of this patent application is incorporated by reference herein.

FIELD

The present invention relates to a method for providing health record data, a non-transitory computer-readable medium having a program element stored thereon that defines a method for providing health record data that can be performed when the program element is executed, and a communication system for providing health record data.

BACKGROUND

Currently in case of an emergency, for example, in case of healthcare problems such as a seizure or collapse which may occur outdoors or in the event of a vehicle accident and when there is a need to request ambulance services and hospital assistance, the subject of the emergency event may be unable to trigger the healthcare system and needs help from third parties. The victim of the accident may also not be able to report the event and to provide information regarding his/her identity, social number and/or Electronic Healthcare Record (EHR).

SUMMARY

I determined that the unknown identity of the accident victim may result in the healthcare professionals being unable to use the time advantage during the transport of the person to retrieve information such as the EHR details of the person in need before the arrival at the hospital. This lack of information may prevent the preparation of necessary medical equipment and the provision of a high-quality healthcare service. Consequently, there is a time response delay to provide the appropriate healthcare schema which can be crucial in cases with high severity and with a high number of emergency events.

Therefore, embodiments of the present invention can be based on the object to provide an efficient communication and information retrieval. In more detail, embodiments can provide an automated mechanism to recognize citizens in need and to provide his/her electronic health records to the appropriate clinic or health center that will serve the citizen.

According to an aspect of the present invention, embodiments of a method for providing health record data and/or for analyzing a call from a user to an operator is provided. For instance, the user is the victim, a third party, a first responder or an emergency care providing person setting up the call. The user tries to gather and/or to collect as much environmental data as possible in order to get data about the accident or the incident and the victim or the person in need. The environmental data may be collected by taking images of the victim via at least one device (e.g. a smartphone, a tablet, other type of communication terminal having a processor connected to at least one camera sensor, etc.) and/or of the environment and/or by evaluating sensors installed in a mobile device.

The method comprises receiving data, such as images which can be triggered automatically by an Internet of Things (IoT) device and/or which can be taken by an officer, e.g. a police officer, of a citizen in need who forwards this to the system for recognizing the user. The IoT device can be a device that includes a processor connected to a non-transitory memory and at least one transceiver.

A call can be used to forward this image of the citizen. The data then may be routed and/or forwarded to a proposed system, such as an operator, e.g. a person receiving the data and/or to a server for automatic data handling. A call may be indicated as an emergency call, for example, by setting an emergency call flag in the data packages associated with this emergency call. This flag may allow for prioritizing data packages belonging to an emergency call when routed through a common communication network together with other less important traffic. The emergency call comprises identification information gathered by the user and/or position information of the user. In an example, the identification information can comprise the severity of the incident. It is assumed that the user and the victim are identical persons and/or in close proximity so that the identification and/or position information is/are corresponding information from the victim. The information gathering may be activated by pressing an emergency button on a mobile device operated by the user. Triggering the emergency button may also set the severity information to a predefined value.

The method further comprises generating a victim dataset from the received information, e.g., from the identification information gathered by the user and/or from the position information gathered by the user and storing the victim dataset in a victim identification database. For generating and/or storing the victim dataset, the receiving device sends and/or routes the received information to a victim dataset generation device. In an example, the victim identification database may be a temporary database where the victim dataset is stored locally for a predefined time, e.g. in a communication system or in a server. The interval during which the information is stored may be the time needed for processing an identity of the victim. The victim identification database may be deleted after the identity of the victim is found in order to guarantee data protection requirements.

The information provided in the call which may be stored in the victim identification database, can allow the method to retrieve, e.g. with an identity recognition device, at least one set of private information based on the victim dataset, wherein the at least one set of private information matches the victim dataset with a predefinable probability. The degree of matching may be determined by employing weight vectors and/or by employing distance vectors. The at least one set of private information may be derived from a plurality of private information stored in a private database.

The method further comprises collecting for each set of the at least one set of private information activity information from a list of activity databases, wherein the activity information is associated with the at least one set of private information and generating for each set of the at least one set of private information at least one set of aggregated information. In an example, the activity information is collected and the at least one set of aggregated information is generated by an identity processing device. The list of the activity database may be a list of addresses of databases which is actually requested. In other words, the identity processing device may retrieve from a list of activity databases the location of a corresponding database and may retrieve the activity information from the corresponding database addressed by the list. The at least one set of aggregated information comprises the at least one set of private information and activity information associated with the at least one set of private information. In other words, the at least one set of aggregated information comprises the private information of the corresponding set enriched with the collected activity information. Activity information may comprise a history of social networks, wherein the history is associated with each of the at least one set of private information, the victim dataset and/or with the victim. In this way a movement profile of the possible victim may be correlated with the location of the incident and in this way the identity of the victim may be confirmed.

After the at least one set of aggregated information is generated, the method comprises selecting from the at least one set of aggregated information a particular set of aggregated information that matches the victim dataset the best. This selection may be made by the identity processing device. A best match may be calculated by using a weight vector. In other words, between the provided at least one set of aggregated information, the particular one set is selected that meets a predefined requirement better than the others.

The method further comprises retrieving health record data from a health record database based on information from the particular best match set of aggregated information. In an example, the health record data is retrieved by a health record evaluation device.

The retrieved health record data is provided by the health record evaluation device, e.g. on an output interface of a communication system and/or on an output interface of the health record evaluation device. In an example, the call may be forwarded to an operator who may answer the call and receives the health record data together with the call. The call may be forwarded to the hospital that owns the health record data. The health record data may be provided as an EHR. The health record data may be stored in an encrypted format in a database.

In this way the method may be used for recognizing a victim and/or for retrieving health record data.

It is to be mentioned that the terms "victim", "private", "activity" in relation to information, dataset and/or database may be seen as names to differentiate the different items as long as no other indication or restriction is provided. The term "private" may indicate that an authorization and/or authentication is necessary to access the data.

A call as used in this text may refer to any data stream. The stream may be a stream generated by a camera, an audio device and/or by an IoT device. The call may be any connection oriented and/or connectionless data communication.

An automated mechanism to recognize citizens in need and to provide his/her electronic health records to an appropriate clinic or health center that will serve the citizen is suggested as well.

Embodiments of the method may be used for identity recognition based on an image and/or a unique feature such as a scar or a tattoo that may be visible on an image of a person in need and/or the victim. It may be seen as a gist of the method to collect as much information of a person who needs to be identified without talking to this person and match the collected information with information that is accessible via private and/or public networks where this person may have left traces in the digital world of communication networks.

In this way it may not be necessary to proactively save any image, profile, EHR or other private data for a long time and consequently data protection concerns may be eliminated. Furthermore, by accessing primarily defined interfaces, such as a RESTAPI (Representational State Transfer Application Programming Interface), substantially no applications and/or services may need to be maintained locally. Thus, a dependency on other apps and/or services may substantially be prevented, and the local administration effort may be kept low since substantially no installation of software on a device is required.

As the face and/or other unique features are always with the person in need, no special equipment and/or special preparation like a special garment with a QR code is required.

With the method it may be possible to create a system covering a secure platform wherein the platform provides a recognition of the identity of people in need, an aggregation of an EHR and/or of medical data, access to a person's identity and/or to the EHR of the person for a medical center. This access may be explored during the transport of the person from the location of the incident to the hospital. The access may be made independently of any user's interaction and may prevent that a person being unconscious cannot be identified.

The substantial fully interaction-free method may also allow for using an integrated temporary smart contract and validator history of all state transactions for security and future use. It may be possible to offer an automated and adaptable solution for any incident, e.g. an earthquake, a vehicle accident or an expandable solution for other cases where the identity recognition of a person is crucial, e.g. robberies or hijackings. In this way it is possible to provide clear instructions for the medical personal about how to react in special situations before the incident happens and the person may not be able to express his or her agreement and/or consensus.

A private database and/or a private server requests authentication and/or authorization before information is provided. A public database and/or public server may be accessed without any legitimization towards the data and/or server. A database may use a blockchain technology, e.g. a linked list of user records which may be administrated in a decentralized way. The database can be stored on non-transitory memory of a computer device that has a processor connected to the memory and at least one transceiver. The database can be stored on memory of the server, for example. Alternatively, the server can include a processor connected to non-transitory memory and at least one transceiver and can be communicatively connected to the computer device that has the database stored thereon to access the database via at least one communication connection between the server and the computer device hosting the database.

A private database may only provide access to a restricted number of people. In order to restrict the access, a private database may have high security levels before allowing access to this data. In an example, a telecommunication provider may offer a predefined interface for selected authorities, like police or hospitals for accessing their data, e.g. location information for their customers. As there is provided highly private data by such databases, a high focus may be put on the authorization and/or authentication. For example, a private database may only grant access after a two-factor authentication process.

In contrast to a private database a social media provider employs substantially publicly accessible databases which may provide access to information without providing any factor for authentication and/or authorization. Public data may also be collected in a search engine and might be easily found. A publicly accessible social network may be a home page, a blog and/or a communication application.

According to a further aspect of the present invention, the method further comprises executing, generating and/or updating a smart contract based on the victim dataset and health record data, wherein the smart contract is a list of instructions which are carried out when loaded to a processor. In an example, the smart contract may be handled by the health record evaluation device and/or the sub-devices of the health record evaluation device.

A smart contract may prevent interaction with an unconscious person as all relevant instructions are coded in the smart contract.

According to another aspect of the present invention, the method further comprises monitoring the execution of the smart contract, e.g. with the health record evaluation device.

According to yet another aspect of the present invention, the victim identification database, the activity database and/or the health record database is/are accessible via an Application Programming Interface (API), e.g. via a RESTAPI.

The use of a predefined API may allow for accessing data from a database without maintaining a special software and/or application.

According to a further aspect of the present invention, receiving the data comprises authenticating and/or authorizing the originator of the data and/or a third party. The user may be a third party like emergency personal and/or the victim himself/herself.

Authenticating and/or authorizing the originator of the call may allow for identifying the identity of a caller and/or of a person close to the caller, e.g., a person being in the vicinity of the caller.

According to yet another aspect of the present invention, the received information from the victim identification database, the activity database and/or the health record database comprises a link, e.g. a URI (Uniform Resource Identifier) or a URL (Uniform Resource Locator) to the location where the respective information is stored and/or the database is based on the blockchain technology.

A hyperlink can keep the volume of the database small and may reduce the information to be stored in a database. By providing links, no duplication of the content is necessary. The blockchain technology may allow for a high integration of the stored information.

According to an aspect of the present invention, the at least one set of private information comprises a list of matched images.

The images provided may have a specific similarity with the person to be identified. Evaluating of further information belonging to each of the images such as activity information within social media networks may help to generate a plurality of criteria to be matched. In this way the probability of identifying the correct person with a correct match may be high. A high detection probability may allow to qualify for accessing private data such as EHRs. The at least one set of private information may be generated in the private database and/or in an identity matching device on the system, e.g. by using a neural network. In one example, substantially all images stored in the private database are transferred to the identity matching device and said device selects the at least one set of private information by comparing substantially all images with the victim dataset and/or with a converted victim dataset. In another example, the victim dataset and/or the converted victim dataset is transferred to the private database and said database compares substantially all images stored in it with the victim dataset and/or with the converted victim dataset and only provides the at least one set of private information that substantially matches the victim dataset and/or the converted victim dataset. The matching device can be the server that hosts the database, the computer device that hosts the database, or another computer device communicatively connected to the server and/or the database that includes a processor connected to a non-transitory memory and at least one transceiver.

According to a further aspect of the present invention, the data is identified as an emergency call by a field in a data package of the emergency call.

The call may be transmitted as data packages, e.g. according to the SIP (Session Initiation Protocol). One of the fields of such a data package may indicate the content which is transported in that package as belonging to an emergency call. In this way a high priority may be allocated to such a data package when routed through a communication network with a high load.

According to another aspect of the present invention, a machine learning (ML) algorithm is used for matching the least one set of private information with the victim dataset.

The ML algorithm and/or a convolution neural network allows finding at least one set of private information, e.g. images of a private database, which is/are with a high degree similar to a victim dataset, e.g. an image of a victim. This may help to retrieve from a plurality of information relevant information that may be worth to have a closer look when finding the identity belonging to the victim dataset.

According to yet another aspect of the present invention, for matching the at least one set of private information with the victim dataset a ML algorithm is used.

A neural network can be trained with a plurality of images from a private database, e.g. from a blockchain network and find from such a plurality of images a list of matched images. Such a list may be comprised in a set of private information. The ML algorithm may be executed locally in a system for communication and/or in the private blockchain database.

According to a further aspect of the present invention, generating a victim dataset comprises using a face recognition process and/or a unique feature recognition process.

Face recognition and/or unique features recognition allows to extract characteristics and/or a dataset of frames of a person in need which can form the basis for a further identity recognition process.

According to yet another aspect of the present invention, the face recognition process and/or a unique features recognition process comprises a correction process.

In an example, filter may be applied to find an area of interest having a unique feature in an image and/or to remove from the area of interest disfigurements such as blood or mud to remove interference that could make a recognition process difficult. Deep learning algorithms may be used to convert the area of interest of the image with the unique characteristics to a file format, e.g. a dataset of frames that can be processed by a succeeding stage, e.g. an identity recognition component and/or a neural network.

According to a further aspect of the present invention, the method comprises fetching the identification information and/or the position information by a device close to the user.

The identification information and/or the position information may be fetched by a mobile device of the victim and/or of the first responder, e.g. a smartphone.

According to another aspect of the present invention, a program element is provided which when being executed by a processor is adapted to carry out the method for providing health record data.

According to yet another aspect of the present invention, a computer-readable medium is provided comprising a program code which when being executed by a processor is adapted to carry out the method for providing health record data.

A non-transitory computer-readable medium may be a floppy disk, a hard disk, a USB (Universal Serial Bus storage device), a RAM (Random Access Memory), a ROM (read only memory) or an EPROM (Erasable Programmable Read Only Memory). A computer readable medium may also be a data communication network, e.g. the Internet which may allow downloading a program code.

According to a further aspect of the present invention, a system for providing health record data. The communication system can include at least one computer device having a processor connected to a non-transitory computer readable medium and at least one transceiver. The system can comprises a receiving device, a victim dataset generation device, an identity recognition device, an identity processing device, and a health record evaluation device. Each of these devices may be defined on a computer device and/or array of computer devices in some embodiments. For example, each of these devices may be different computer devices that are communicatively connectable to each other via communication connections (e.g. at least one network connection, etc.). As another example, a combination of these devices can be included in a single computer device or a plurality of computer devices that are communicatively connected to each other.

The receiving device is adapted for receiving the data, wherein the data comprises identification information gathered by a user and/or the position information of the user.

The victim dataset generation device is adapted for generating a victim dataset from the identification information of the user and/or from the position information of the user and for storing the victim dataset in a victim identification database.

The identity recognition device is adapted for retrieving from a private database at least one set of private information based on the victim dataset, wherein the at least one set of private information matches the victim dataset with a predefinable probability.

The identity processing device is adapted for collecting for each set of the at least one set of private information activity information from a list of activity databases, wherein the activity information is associated with the at least one set of private information and wherein the identity processing device is further adapted for generating for each set of the at least one set of private information at least one set of aggregated information. The at least one set of aggregated information comprises the at least one set of private information and activity information associated with the at least one set of private information.

The identity processing device is adapted for selecting from the at least one set of aggregated information a particular set of aggregated information which matches the victim dataset and/or a converted victim dataset the best.

The health record evaluation device is adapted for retrieving health record data from a health record database based on information from the particular best matched set of aggregated information and for providing the health record data, e.g. in form of an EHR.

It has also to be noted that aspects of the invention have been described with reference to different subject-matters. In particular, some aspects have been described with reference to apparatus type claims whereas other aspects have been described with reference to method type claims. However, a person skilled in the art will gather from the above and the following description that, unless other notified, in addition to any combination between features belonging to one type of subject-matter also any combination between features relating to different types of subject-matters is considered to be disclosed with this text. In particular, combinations between features relating to the apparatus type claims and features relating to the method type claims are considered to be disclosed.

Other details, objects, and advantages of the telecommunications apparatus, system, device, non-transitory computer readable medium, and method will become apparent as the following description of certain exemplary embodiments thereof proceeds.

BRIEF DESCRIPTION OF THE DRAWINGS

The invention and embodiments thereof will be described below in further detail in connection with the drawing(s).

The illustration in the drawings is schematic and may not be to scale. In different drawings, similar or identical elements are given the same reference numbers.

Figure 1:
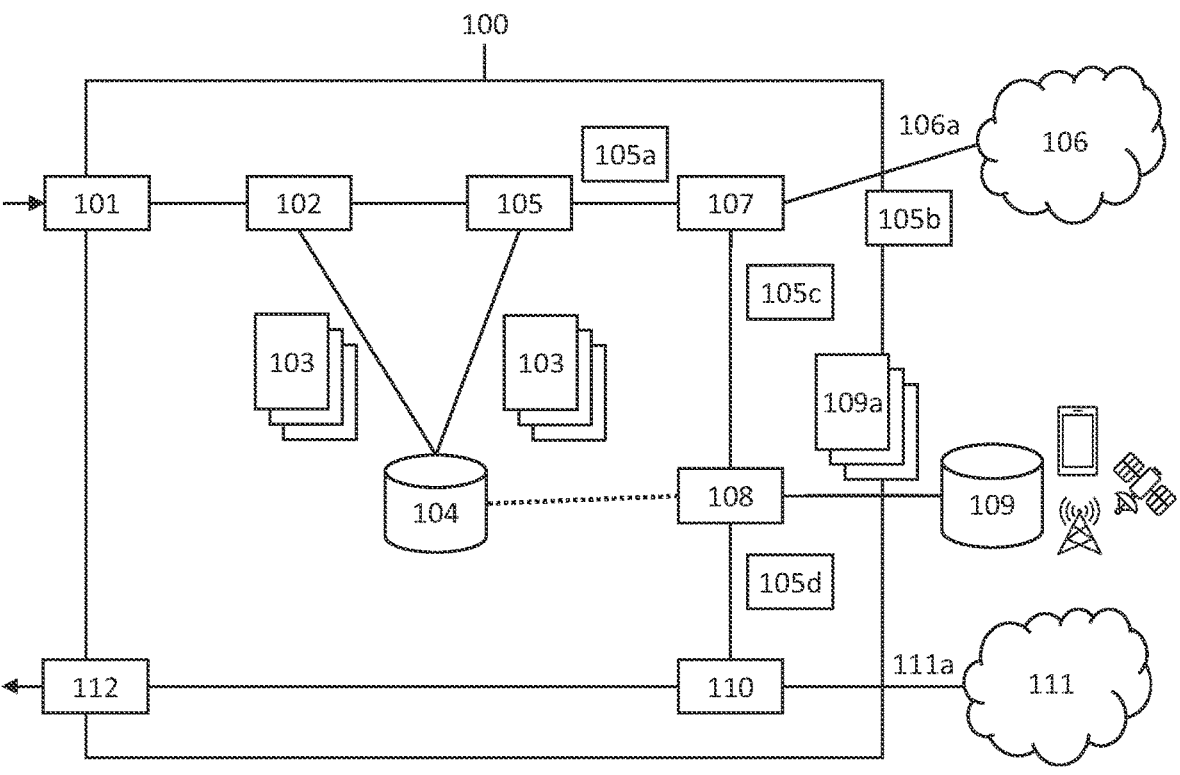
FIG. 1 shows a block diagram of a system for providing health record data according to an exemplary embodiment of the present invention.

Reference numerals used in the drawings include:

100 communication System
101 receiving device
101a PSAP (Public Safety Answering Point)
101b event processing device
101c listener
102 victim dataset generation device
103 victim dataset
104 victim identification database
105 face recognition/unique feature recognition device
105' face recognition device
105" unique feature recognition device
105a converted victim dataset
105b plurality of private information
105c set of private information
105d particular set of aggregated information
106 private database
106a database interface of private database
107 identity recognition device
107' match evaluation device
107" identity provision device
108 identity processing device
108a Identity of recognized person selecting sub-component 109 activity database
109a activity information
110 health record evaluation device
110a health record requesting device
110b contract maintenance device
110c validation device
111 health record database
111a database interface of health record database
112 output interface
201 person reporting an incident
202 first responder
601 neural network
S401-S709 stages

DETAILED DESCRIPTION

FIG. 1 shows a block diagram of a system 100, e.g. a communication system, for providing health record data according to an exemplary embodiment of the present invention. In an example, the communication system 100 is adapted for routing a call from the user to an operator (not shown in FIG. 1). The method may be used for recognizing a person, a user and/or a victim. The method may also be used for routing a call from a user to an operator.

The system 100 comprises a receiving device 101, a victim dataset generation device 102, an identity recognition device 107, an identity processing device 108 and a health record evaluation device 110. As discussed above, each of these devices can include a processor connected to a non-transitory memory and at least one transceiver and can be communicatively connected to each other via a network connection. Alternatively, each of these devices can be included in a communication apparatus having a processor connected to a non-transitory memory and at least one transceiver that can be communicatively connected to user devices and other devices via at least one network connection.

The receiving device 101 is adapted for receiving the call and/or the stream from the user (not shown in FIG. 1). The call originates from a victim and/or a first responder and comprises identification information and/or position information gathered by the user and/or position information of the user. For example, the call comprises an image and/or a stream of the victim or person in need.

The victim dataset generation device 102 is adapted for generating a victim dataset 103 from the identification information of the user and/or from the position information of the user and for storing the victim dataset 103 in a victim identification database 104.

The identity recognition device 107 is adapted for retrieving at least one set of private information 105c from a private database 106 based on the victim dataset 103 and/or a converted victim dataset 105a, wherein the at least one set of private information 105c matches the victim dataset 103 with a pre-definable probability.

In order to retrieve the at least one set of private information 105c from the private database 106 the victim dataset 104 and/or the identification information 103 may be converted into a format 105a that can be used for retrieving at least one set of private information 105c. The least one set of private information 105c may be retrieved inside the identity recognition device 107 and/or inside the private database 106.

For preparing the victim dataset 103 for identity recognition, a pre-processing method is used such as a face recognition and/or a unique feature recognition. The pre-processing stage 105 provides the converted victim dataset 105a that can be transmitted to the identity recognition device 107. In an example, the converted victim dataset 105a is provided in form of a dataset of frames 105a. Even if there is no official dataset, each authority such as government agency, has a database of images of all citizens. For example, such a database is created when an ID card, social security card, and/or a passport is issued by an authority. The aggregation and correlation of, for example, these images 105b periodically result in the creation of such a data set 106. The converted victim data set 105a which is generated from the victim data set 103 is analyzed during the identity recognition and/or during an identity recognition phase.

During the identity recognition phase, in one example, a plurality of private information 105b is forwarded via API 106a or RESTAPI 106a into the identity recognition device 107 where this private information 105b is matched with the victim data set 103 and/or with the converted victim dataset 105a. At least one set of private information 105c is generated inside the identity recognition device 107.

In another example, during the identity recognition phase the database interface 106a, e.g. an API or RESTAPI 106a of the private database 106 is addressed with the converted victim data set 105a or the converted image data set 105a. As a result, the information retrieved from the private database 106 comprises at least one set of private information 105c. The at least one set of private information 105c is selected from a plurality of private information 105b offered by the private database 106.

The selection of the at least one set of private information 105c may be supported by a neural network inside the identity recognition device 107 and may provide a certain number of sets of private information 105c which meet a pre-defined probability level for the degree of matching the converted victim data set 105a and/or the victim dataset 103.

The selected at least one set of private information 105c is forwarded to an identity processing device 108.

The identity processing device 108 is adapted for collecting for each set of the at least one set of private information corresponding activity information 109a. The activity information 109a is collected from at least one activity database 109 and/or from a list of activity databases 109, wherein the activity information is associated with the at least one set of private information 105c. The identity processing device 108 is further adapted for generating at least one set of aggregated information for each set of the at least one set of private information 105c (not shown in FIG. 1). The at least one set of aggregated information comprises the at least one set of private information 105c and activity information 109a associated with the at least one set of private information 105c. The volume of activity information 109a may depend on the activity in social networks and/or the use of data collecting devices. A social media influence who is very open with data provision and uses gadgets like mobile phones, wearable device and/or data driven cars may generate more data in an activity database 109 than a person who may be very restricted in providing data.

The identity processing device 108 is further adapted for selecting from the at least one set of aggregated information a particular set of aggregated information 105d which matches the victim dataset 103 and/or the converted victim dataset 105a the best and to forward the best match 105d to the health record evaluation device 110. The particular set of aggregated information 105d is a single set of information so that an unambiguous result may be provided. If none of the at least one set of aggregated information matches the converted victim dataset 105a sufficiently clear no result is provided.

The health record evaluation device 110 is adapted for retrieving health record data from a health record database 111 based on the information from the particular best matching set of aggregated information 105*d*. The health record database 111 is accessed via database interface 111*a* of health record database 111 which may be an API such as RESTAPI.

The health record evaluation device 110 is adapted for providing the health record data, e.g. in form of an EHR. The health record data may be provided via an output interface 112 such as a network interface. In an example, the health record data is packed into the call and the call is forwarded to an operator who may coordinate the transport of the victim to a hospital.

In emergency cases where a person in need and/or a victim has been seriously injured or is unconscious the system 100 may help to disclose the identity of this person during the time until the person reaches the emergency center and/or hospital or is recognized by a person who knows the person in need. The delay that otherwise may arise for providing personalized healthcare treatment could be reduced. Such a delay may affect the recovery process. Reducing the delay may potentially save a victims' life as the recognition of identity details of a person such as the person's identity and social security number may be automated. Furthermore, the process to aggregate and integrate a person's distributed EHR may be automated. In addition, the delivery of the aggregated information to the corresponding hospital that will serve the person in need may be automated and therefore accelerated.

In cases of massive emergency disasters, e.g. earthquakes, a volcano eruption, and bomb explosions where hundreds of people are injured and transferred to different hospitals, the healthcare system may be supported to handle more cases if automatic identity recognition is used. The time response delays may be kept low, and the healthcare professionals are not distracted from delivering personalized services to the victim by identifying a person.

Moreover, having all the available information in place may support healthcare professionals and systems in providing efficient pre-hospital triage guidelines and support practitioners' decision-making in emergency situations.

The person's identity recognition and integration of his/her EHR may become important for saving their lives and provide high quality personalized services in different scenarios.

In one example, a cyclist may have an accident in the center of a town. The cyclist may have crashed onto a vehicle and is lying unconscious on the road. Nearby, there is no person around who has any knowledge about the person in need to report his/her identity. The first responders, the ambulance service and the hospital are informed about the accident. If the person has not proactively saved any information about his/her identity and profile, there might be a gap between the time the emergency center will be informed about the incident and the time the person receives the treatment. Using the system 100 may reduce the gap that otherwise may occur due to the time delay to validate his/her identity, request and retrieve the entire or partial EHR and provide the personalized healthcare schema. It may be possible to quickly find out that the victim is hypersensitive to certain medications and to support the first responders and the hospital with this information to be aware of possible negative and/or allergic reactions and plan a treatment accordingly.

In another example, a massive emergency incident, e.g. a fire, a bomb explosion or an earthquake happens in a crowded place such as a mall. Under such circumstances dozens of injured people suddenly need care and among the people in need may possibly be some pregnant women. Based on any action plan such as triage guidelines, first responders may need to apply different protocols and may need to treat the pregnant women with different priorities. The system 100 allows to provide information about the profile and specific situation of people in need and use that information for the guidelines.

Determining the identity of a person and correlate it with the EHR has shown a significant improvement of the response time in crucial events. The suggested system 100 provides a generic platform which can automatically identify a person's identity, by means of providing a name, surname, and social number. The platform may support requesting, retrieving and integrating the individual's EHRs and profile, as well as proactively providing all the available information to the corresponding emergency center or hospital. Such system 100 may support healthcare professionals in their decision-making process in emergency situations, decrease the response time and may save lives.

The system 100 may be seen as an automated platform and/or an end-to-end solution which helps recognizing the identity of a person in need, triggers the mechanism for requesting and retrieving the person's distributed healthcare records and EHR as well as for forwarding the available information to the emergency system or hospital and pre-hospital professionals who treat this person in need.

Thus, an automated platform is provided which recognizes a person's identity and triggers the aggregation and retrieval process of profile data and EHR information related to recognized persons which will then be forwarded to the emergency system responsible for the current incident. It may combine a plurality of identification devices and/or identification methods in order to increase the probability of a match between the gathered information from a person in need and the stored information of huge databases. And in this way, providing an EHR that belongs to the person to be identified with a very high grade of probability.

The proposed system 100 provides a common platform that automatically recognizes the person in need, correlates results of identification methods such as face recognition and unique marks recognition with the person's identity. The system 100 requests, retrieves, integrates, and provides a healthcare profile and/or EHR of the person in need to the emergency personal before the person in need reaches the emergency center. In other words, an "a priori" identification, search, integration, and provision of the appropriate data may be provided which results in a personalized healthcare treatment with a high quality and substantially without uncertainties.

Figure 2:
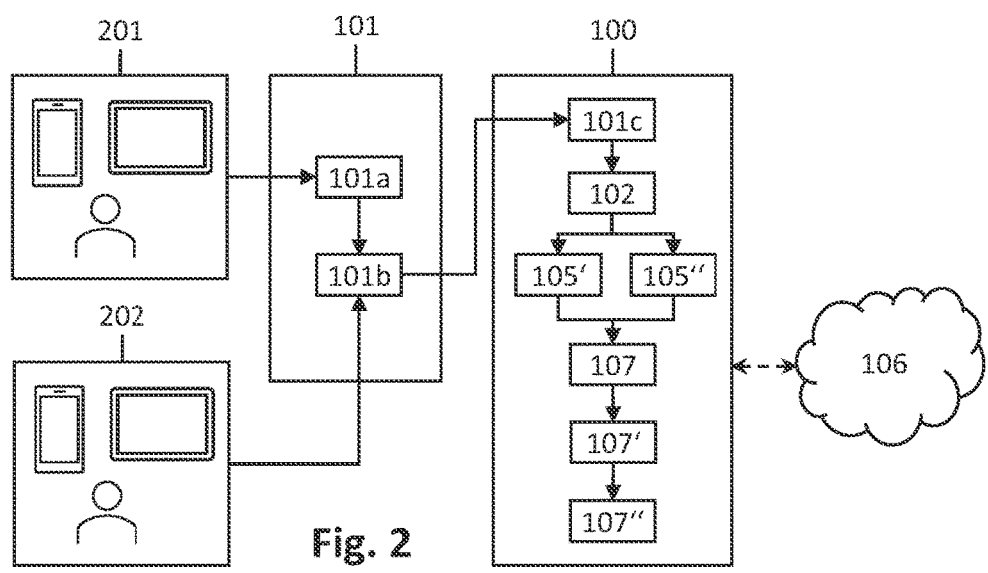
FIG. 2 shows a structural overview diagram of an identity recognition component for a method for providing health record data according to an exemplary embodiment of the present invention.

FIG. 2 shows a structural overview diagram of an identity recognition component for a method for providing health record data according to an exemplary embodiment of the present invention.

The system 100 can be triggered either by a person reporting the incident 201 and/or, by the victim 201 or by the first responder 202 who reaches the place of the emergency scene. The reporting of the incident can be provided via a user device used by that person. The user device can be, for example, a smart phone or other type of communication terminal having a processor connected to a non-transitory memory and at least one transceiver (e.g. s cellular phone, a tablet, a laptop computer, etc.). Upon an emergency event, the person reporting the incident 201 may use his/her mobile device to take a photo of the incident and send it to the Public Safety Answering Point (PSAP) 101*a* and at the same time providing the location and the severity of the incident. In an example, the first responder takes a photo or generates another medial file and uploads the photo or other media file, image and/or video of the person in need to the receiving device 101. In this way a call and/or stream may be routed from the user to an operator who may handle this emergency. It should be appreciated that the PSAP can be a communication device having a processor connected to a non-transitory memory and at least one transceiver.

The PSAP 101a, which may be comprised in the receiving device 101, forwards the image via an event processing device 101b to the system 100. Additionally, the first responder 202 who reaches the incident scene may use his/her mobile device to take a photo of the person in need to send it directly to the event processing device 101b by surpassing the PSAP 101a. The event processing device 101b is also a part of the receiving device 101.

The image or other media file may be embedded in a call and is forwarded via the event processing device 101b to a listener 101c and to a data processing stage 102, e.g. a victim dataset generation device 102.

The system 100 uses ML algorithms in a face recognition device 105' to process the image and to detect the face of the person in need and/or uses ML algorithms in a unique feature recognition device 105" to detect any special characteristics that may be unique for a person, e.g. a tattoo or a scar. The devices 105', 105" help to isolate and crop the face from the whole picture and to locate an area of the unique characteristics and/or unique features. In case of injuries, detection algorithms are applied in the face recognition device 105' and/or in the unique feature recognition device 105" to restore the affected parts of the image of the victim such as scratches, blood, in other words, to remove characteristics caused by the accident.

The output of the identity recognition process is forwarded to the identity recognition component 107. The identity component 107 interacts with a database 106 where encrypted images from all citizens are stored, e.g. in a blockchain network. In order to get the dataset of the images and perform an image recognition, deep convolution neural algorithms are used. The probability of a match of the encrypted images with the recognized image is measured inside the identity component 107 by detecting the smallest distance between corresponding features in the images by using a match evaluation device 107'. A good match is indicated by a small distance value and/or a high accuracy value. Once the smallest distance of the image under recognition with the dataset has been identified, the system 100 uses the information from the blockchain network 106 to retrieve the identity of the person in need in an identity provision device 107". The identity provided by the identity provision device 107" may also be a set or list of images that match the recognized image with a predefined probability.

Upon the identity recognition of the person in need in the identity recognition device 107, 107', 107", the system 100 interacts with another private blockchain network 111 (not shown in FIG. 2) in which the medical and paramedical organizations, clinics, hospitals, and healthcare providers participate in order to request the EHR and profile information for the identified person. The proposed system 100 sends a request with encrypted data of the person in need to the hospitals and medical centers that participate in the private blockchain network 111 in order to mine the distributed medical data. The participants of the blockchain network 111 use their private keys to decrypt the identity of the person in need and answer to the request with a positive or negative answer.

In case of a negative answer, the access to the blockchain network 111 is denied.

In case of a positive answer, e.g., the person is found in the EHR network 111, the URLs with the location of the information are also provided. The EHR aggregator component stores the aggregated information which does not contain actual files and medical data but a complete list with all the URLs and with all the organizations where the data is located. Then, the system 100 interacts with the PSAP 101a to request and receive the authorized responsible PSAP for the person in need for forwarding the call and/or the retrieved information (not shown in FIG. 2). Based on this information a new smart contract between the hospital responsible for the person in need and the institutes that have stored the EHR data for this person is signed.

The system 100 creates the smart contract, defining the rules regarding the permitted and prevented actions in order to authorize the hospital that will serve the person in need to have access to the provided URLs in order to read, modify and save the EHR. This new smart contract is supplied to the private blockchain network 106, 111 operated by the healthcare organizations. All the transactions are a set of asset key-value pairs that are committed to the system to track the process and provide or restrict access to this data.

Figure 3:
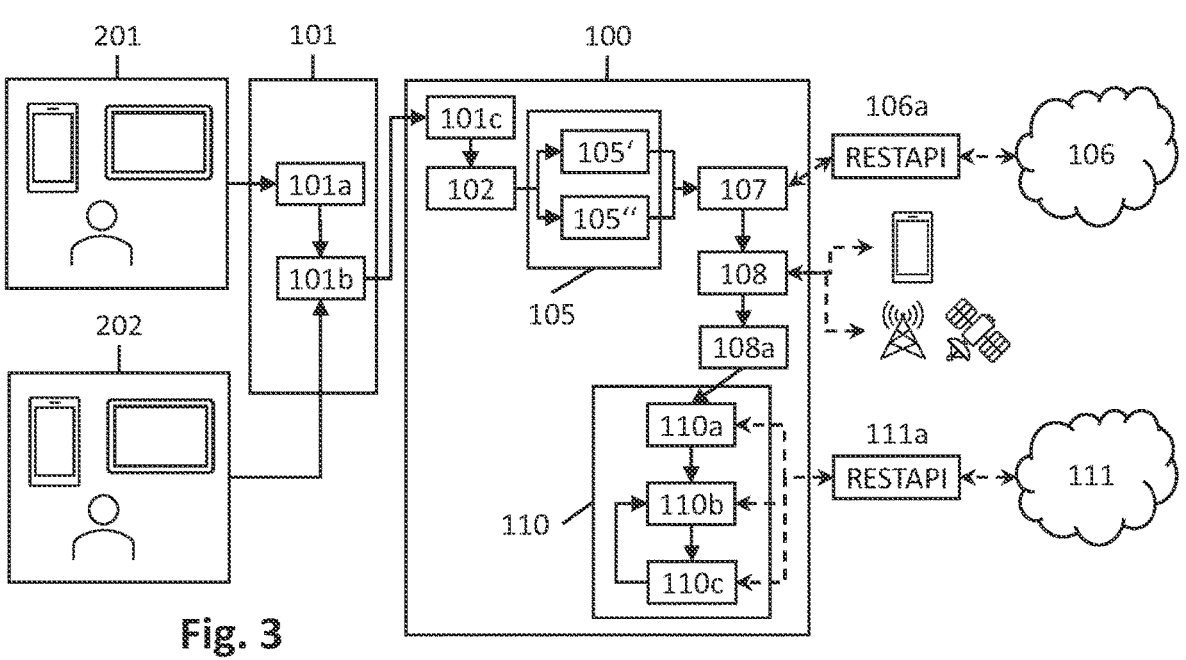
FIG. 3 shows a structural overview diagram of the system for a method for providing health record data according to an exemplary embodiment of the present invention.

FIG. 3 shows a structural overview diagram of the system 100 for a method for providing health record data according to an exemplary embodiment of the present invention.

The proposed system can be triggered either by the first responders 202 who reach the area of the emergency incident or by the PSAP 101a whenever a caller 201 reports an emergency incident and provides a media file such as an image and/or a video of the person in need. The entities 201, 202 who trigger the system 100 may use their portable devices, e.g. their smartphone or tablet to take a photo or video of the person in need.

The system 100 comprises an entry point in form of receiving device 101. Receiving device 101 comprises the listener 101c which is up and running and is responsible to receive the provided media file. The media file may be uploaded to the listener 101c in a data stream and/or in a call. The listener 101c may be implemented as a server listening to a network interface, to a network port and/or to a network socket. The system 100 interacts with two independent blockchain networks 106, 111 using a client application interface 106a, 111a, e.g. realized as a RESTAPI. The client application interface 106a, 111a allows the system 100 to submit transactions to the blockchain networks 106, 111 for using services such as request images, personal data, EHR and medical data. The blockchain network 106, 111 has been selected to ensure that the system is immutable as the images, the owners of the images and their EHRs cannot be changed. In other words, the use of a decentralized blockchain network 106, 111 may ensure the integrity of the data stored therein, e.g. the images, the owners of the images and the EHRs belonging to the owners of the images.

The listener 101c can be implemented as a server which is substantially permanently running and ready to accept media files from the user 201 and/or first responder 202. The listener 101c manages the authentication and authorization of the sender, e.g., the user 201 and/or first responder 202 of the media file and its contents. In an example, the media file, e.g. a video stream and/or an image, is transported in a call, e.g. in a Session Initiation Protocol (SIP) and/or in another Voice over Internet Protocol (VoIP).

In cases where the originator 201, 202 of the media file may not be able to be certified as to be authorized or validated to send messages to the system 100, in particular the listener 101*c* informs the sender 201, 202 of the media file about the cause of the failure.

In cases where the transmission of the media file is valid, the listener 101*c* forwards the media file of the sender 201, 202 to the data processing component 102, e.g. the victim dataset generation device 102.

The data processing component 102 is adapted for data processing. Upon reception of the media file from the listener 101*c*, the data processing component 102 or the victim dataset generation device 102 prepares the media file for applying ML algorithms. The ML algorithms help detecting substantially all faces included in the media file, e.g. in an image and/or in a video.

For the purpose of identity recognition, a victim dataset 103 is generated and stored in a victim identification database 104 (not shown in FIG. 3). The victim dataset 103 can be accessed by the face recognition/unique feature recognition device 105 which is adapted to detect the person in need and to isolate this person on the image and/or video.

If a video file is provided, the data processing component 102 converts the snapshot of the detected person in need to a static image file. Afterwards, it stores temporarily the image depicting the person in need in the victim identification database 104. For security and recovery purposes the data is stored until the identity of the person has been examined and the incident has been released. The victim dataset 103, e.g. the image file, is forwarded simultaneously to the face recognition device 105' and/or to the unique feature recognition device 105".

The health record evaluation device 110 comprises a health record requesting device 110*a*, a contract maintenance device 110*b* and a validation device 110*c*. The health record requesting device 110*a* is adapted for retrieving information from a database 111, the contract maintenance device 110*b* is adapted for creating and/or updating a contract, e.g. a smart contract, and the validation device 110*c* or validator 110*c* is adapted for verifying and/or ensuring that the terms of the contract are kept and not violated.

The request EHR and medical info component 110*a* or the health record requesting device 110*a* uses the social number and/or a social security number of the identified person to request the person's EHR and medical data from a health record database 111, e.g. a public and/or a private blockchain network in which the medical and paramedical organizations, clinics, hospitals, and healthcare providers participate.

The private data, e.g. social security number, of the person whose identity is recognized and who potentially is the victim, is provided from the identity processing device 108 and is encrypted. The interaction with the blockchain network 111 is carried out via a client application interface 111*a*, e.g. based on RESTAPI 111*a*. The system 100 sends requests via this interface 111*a* and receives responses to these requests via this interface 111*a*.

Similar to the RESTAPI interface 106*a* of the private database 106, also the RESTAPI interface 111*a* of the heath record database 111 provides an interface to register, subscribe to and interact with the public healthcare blockchain network 111. This public healthcare blockchain network 111 comprises, for example, hospitals, clinics, healthcare professionals, medical and paramedical organizations that have each locally stored citizens EHRs, laboratory examinations and medical profiles and connect the locally stored citizens EHRs via the public healthcare blockchain network 111.

The blockchain network 111 ensures that the system is substantially immutable as the EHR, and medical profiles are sensitive data. The blockchain technology guarantees the integrity of the stored data. Only authorized and authenticated users are permitted to have access to the blockchain network 111. Moreover, the content of the blockchain network 111 cannot be changed. Each medical information is encrypted and validated by the members of the blockchain network 111. The participants of the blockchain network 111 use their private keys to decrypt the identity of the person and encrypt their answer to the request with a positive or negative answer.

Blockchain miners are used to retrieve the distributed medical data and profiles for the identified person. The RESTAPI 111*a* enables the system 100 to submit transactions to the blockchain network 111 for using and/or consuming services such as requesting, receiving data, providing new contracts, and contributing to the validation of the new or updated submitted contracts, e.g. smart contracts.

In case of a positive answer from the RESTAPI 111*a*, e.g., requested information is available on the blockchain network 111, the URLs pointing to the location of the requested information are provided together with the positive response. The health record requesting device 110*a* aggregates and stores these responses which only comprise location information in form of a complete list of URLs and a list of the corresponding organizations where the data is located but wherein the responses neither comprise the actual files themselves nor medical data.

The health record requesting device 110*a* aggregates the positive responses and forwards them to the create/update contract component 110*b* also named contract maintenance device 110*b*.

The system 100 interacts with the PSAP 101*a* to request and receive the authorized responsible care unit for the person in need, e.g. a hospital or a clinic. Based on the information gathered by the health record requesting device 110*a*, the health record requesting device 110*a* creates a new smart contract between the identified person's health insurance, the hospital responsible for the person in need, the medical organizations that have positively responded and that own the EHR and medical data for this person. This contract defines the rules regarding the permitted and prevented actions and authorizes the care unit, e.g. the hospital which will serve the person in need to access the provided URLs in order to read, modify and save the EHR.

This newly created smart contract is forwarded to the public healthcare blockchain network 111. The involved parties and/or participants in cooperation with the smart contract executor and/or operator of the blockchain network monitor, analyze, improve, and optimize the submitted smart contract and consent to the deployment and execution of the smart contract to the blockchain runtime environment.

Based on this newly created smart contract, the responsible care unit uses its public and private keys to gain access to the encrypted EHR and medical records of the identified records. All the transactions are a set of asset key-value pairs that are committed to the system to track the process and provide or restrict access to this data.

The validation device 110*c* or validator 110*c* is adapted for verifying and/or ensuring that the terms of the contract are kept and not violated. The validation device 110*c* interacts with the responsible unit and the blockchain network 111 in order to track its actions. In case the contract is violated, the validation device 110*c* restricts access to the blockchain network 111 and to the data of the person in need. In this context, the validation device 110*c* is triggered to modify the rules.

This integrated system 100 allows for recognizing a person in need and providing his/her profile and/or EHR to medical professionals before the person in need arrives to the emergency system.

The system 100 provides a common platform that automatically recognizes a face and unique features, e.g. scratches or tattoos and matches them with a person's social identity and/or with a person's activity data. The system 100 searches, aggregates, and provides the integrated EHR and profile of the recognized person as well as it forwards the related information to the emergency system, the emergency center, the healthcare system and/or the hospital which will be responsible for handling the incident. The routing of a call and/or of information to such an entity, system or center is controlled by the different components of the system 100. This integrated system 100 allows for recognizing a person in need and providing his/her profile and/or EHR to medical professionals before the person in need arrives at the emergency system.

The system 100 responds with a positive or negative answer and/or with a percentage of match, in case the face of a person has been identified from a pool of images 105*b*. In addition to this feedback, the system 100 provides other related private information regarding the identified person, such as his/her identity, name, insurance number, social number and/or social security number.

The system 100 also combines identity recognition with searching and retrieving the patient's distributed EHR. It informs medical professionals about the identity of the person they are going to treat during the time the patient or victim is on the way to the hospital and the system 100 also retrieves this persons' medical data.

By combining the system 100 with the capability of contract handling, the system 100 can access stored information such as access permissions which the person in need has proactively assigned to all emergency systems to get his/her data by means of read and write.

The system 100 prevents a preparation like proactively printing QR (Quick Response) codes to the garment of the person in need wherein the QR code comprises information regarding his/her EHR. QR codes may require to always position the garment with the QR code in a visible place near the person. The QR code may frequently need to be updated by the treating physician, otherwise the information would be obsolete.

The system 100 offers a common platform that automatically recognizes the person in need, correlates the recognized face and unique marks to the person's identity, requests, retrieves, integrates, and provides their healthcare profile and EHR to the emergency system and/or to the health care center that has been selected to treat the person before the person reaches the emergency center. This "a priori" identification, search, integration, and provision of the appropriate data may provide the benefit of a qualitative personalized healthcare treatment with substantially no uncertainties.

Figure 4:
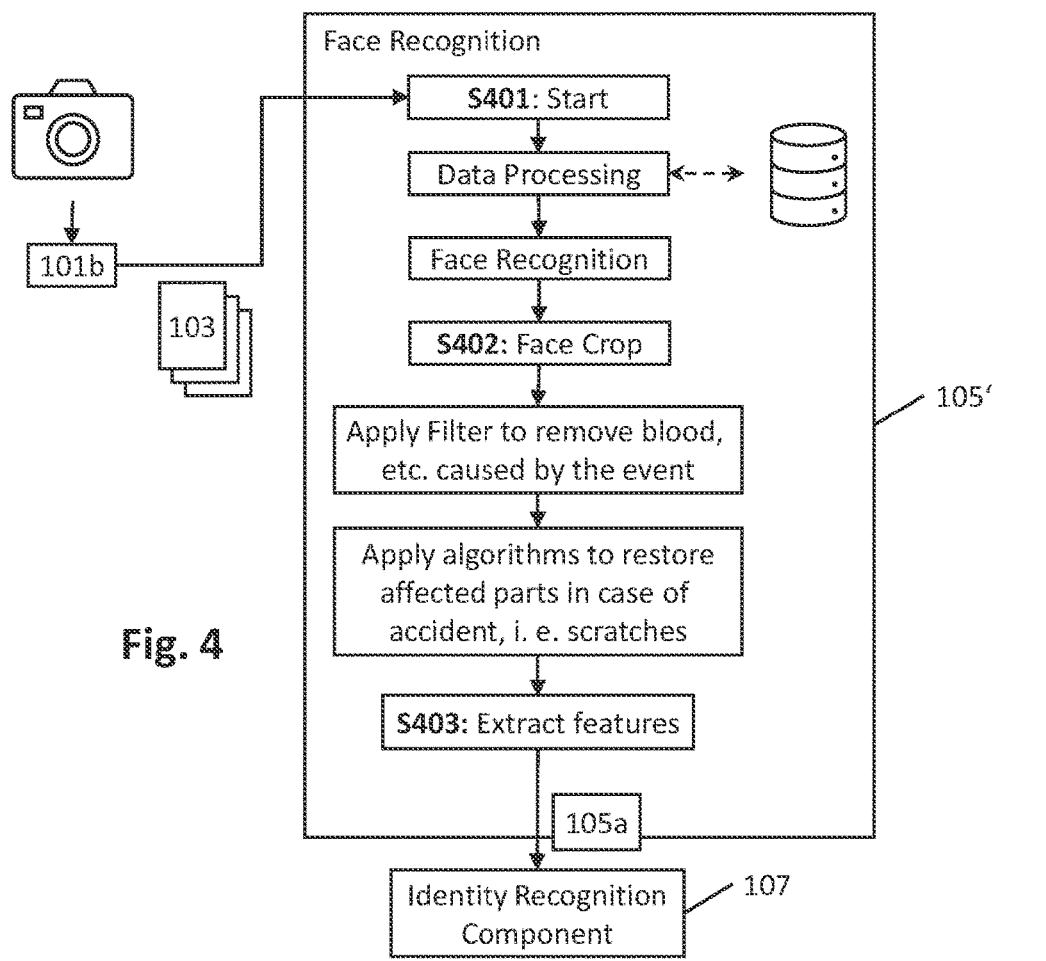
FIG. 4 shows a schematic flowchart for a face recognition process inside a face recognition device according to an exemplary embodiment of the present invention.

FIG. 4 shows a schematic flowchart for a face recognition process inside the face recognition device 105' according to an exemplary embodiment of the present invention.

The face recognition process, which is applied in the face recognition/unique feature recognition device 105, receives the media file and/or the victim dataset 103 from the event processing device 101*b* and/or from the victim identification database 104 (not shown in FIG. 3) and executes in stage S401 an image content analysis and pattern recognition algorithm in order to detect the face of the person in need.

The face is cropped in stage S402 in order to eliminate interference that are not necessary for further processing.

Filters are applied to the cropped face in order to remove any disfigurement such as blood, mud from the face. Moreover, algorithms are used to restore any face features affected by the incident such as recently inflicted scratches or blood. The features of the face are extracted and normalized. Deep learning algorithms are used to convert the final facial image to a dataset of frames 105*a* and/or to a converted victim data 105*a*. The converted image data 105*a* and/or extracted features are provided in stage S403 and forwarded via an output interface of face recognition device 105' to the identity recognition device 107.

The converted image data 105*a* are imported to a neural network inside the identity recognition device 107.

Figure 5:
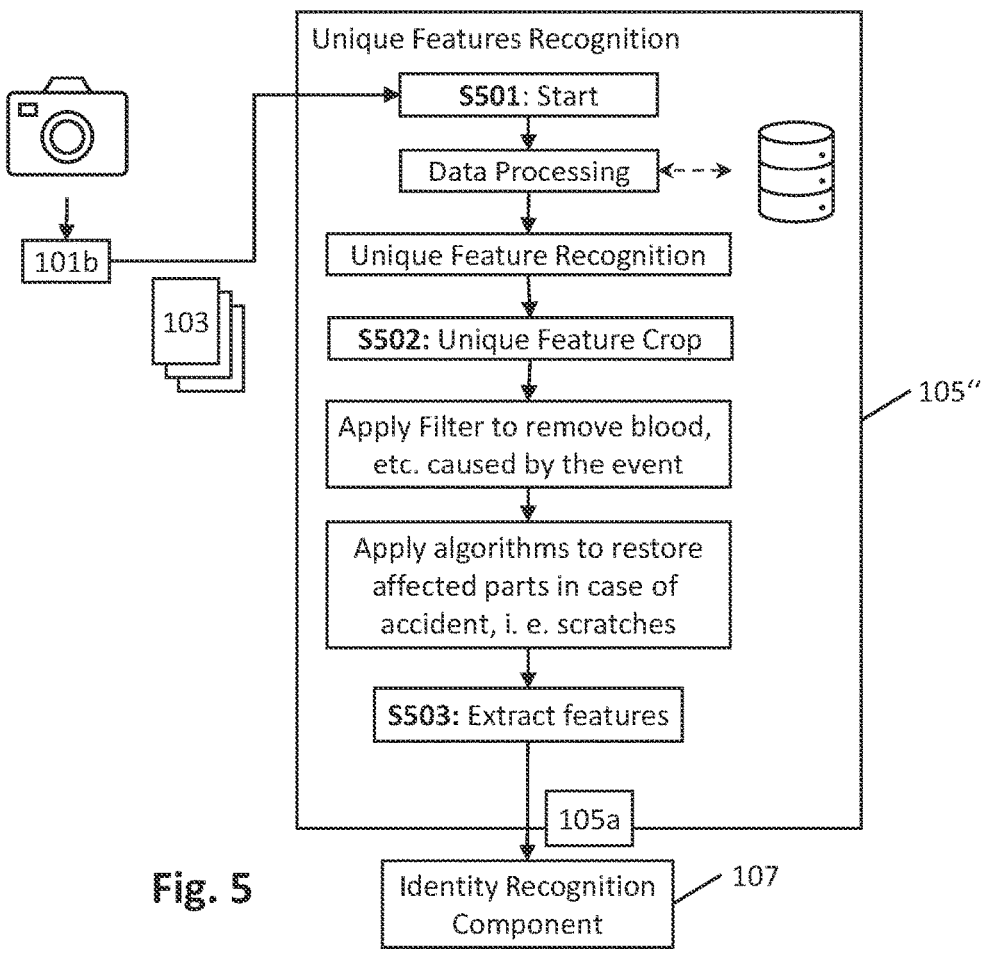
FIG. 5 shows a schematic flowchart for a unique feature recognition process inside the unique feature recognition device according to an exemplary embodiment of the present invention.

FIG. 5 shows a schematic flowchart for a unique feature recognition process inside the unique feature recognition device 105" according to an exemplary embodiment of the present invention.

The unique features recognition process which is applied in the face recognition/unique feature recognition device 105 (not shown in FIG. 5), receives the media file and/or the victim dataset 103 from the event processing device 101*b* and/or from the victim identification database 104 (not shown in FIG. 3) and executes in stage S501 an image content analysis and pattern recognition algorithm for detecting special characteristics of the person in need such as old scars or tattoos. It is to be noted that at this stage, the unique features recognition process does not have any information about the person in need. Therefore, it is to be noted that old scars and/or old tattoos or other special characteristics are analyzed based on typical parameters for such features but not from a knowledge base about the person. The unique feature(s) is/are cropped in stage S502 in order to eliminate interference that are not necessary for further processing.

Filters are applied by the unique feature recognition process for removing any disfigurement such as blood or mud from the area of interest which comprise(s) the detected feature(s). Deep learning algorithms are used to convert the area(s) of the image which comprises the identified unique characteristic(s) and/or the identified unique features to a dataset of frames 105*a* and/or to a converted victim data 105*a*.

The converted victim data 105*a* and/or extracted features are provided in stage S503 and are passed via an output interface of the unique feature recognition device 105" to the identity recognition device 107.

Figure 6:
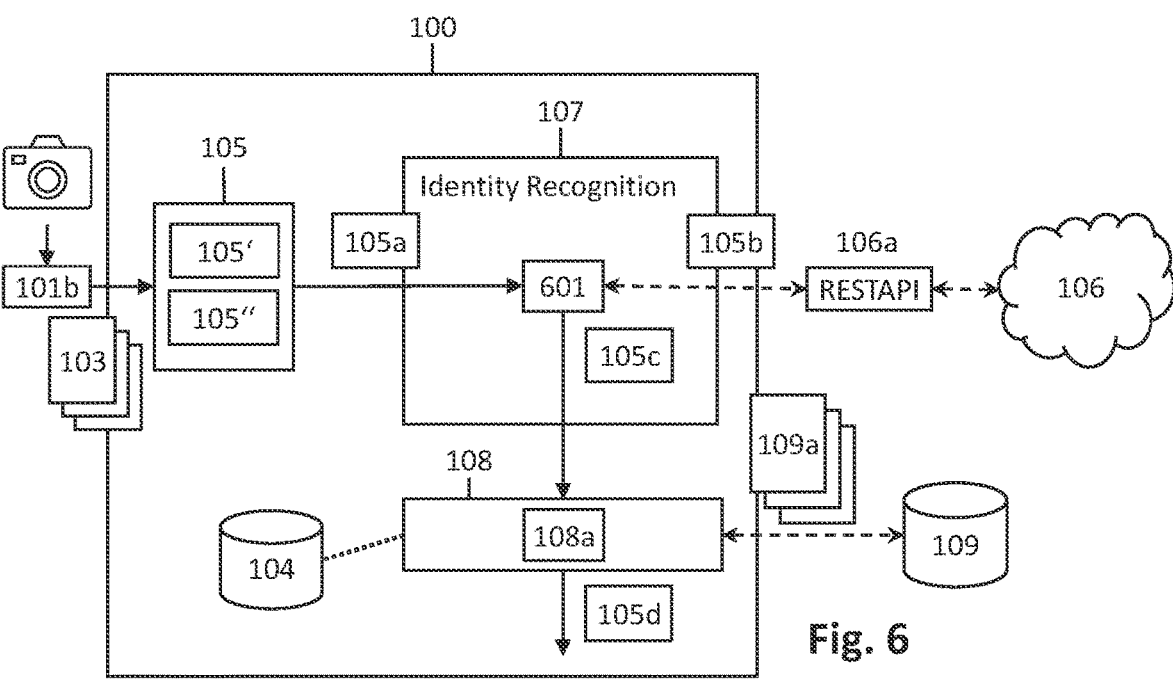
FIG. 6 shows a schematic flowchart of an identity recognition device according to an exemplary embodiment of the present invention.

FIG. 6 shows a schematic flowchart of an identity recognition device 107 according to an exemplary embodiment of the present invention.

The identity recognition device 107 or identity recognition component 107 receives the datasets of the frames 105*a* or converted victim data set 105*a* from the face recognition/ unique feature recognition device 105, in particular from the face and unique characteristics recognition components 105', 105", respectively.

The identity recognition component 107 interacts with a private blockchain database 106 via the REST API 106*a* where encrypted images 105*b* and/or a plurality of private information 105*b* from substantially all citizens registered in a certain area are stored. Either in the identity recognition device 107 or in the private database 106 a selection is made in order to reduce the plurality of private information 105*b* of the private database 106 to a reduced set of private information 105*c* and/or to a reduced dataset 105*c* of images.

In one example, the identity recognition device 107 sends a request to the private blockchain network 106 to retrieve the images of the citizens stored in its database. The response comprises an image key and a cipher text. The image key is used to handle scrambled image frames 105*b* of the citizens which will be used as a training set for a neural network 601 used inside in the identity recognition device 107. Since, the frames are in order, the cipher text is used to decrypt the image frames. Data mining techniques are used to derive knowledge of the data.

The content of the data derived from the decrypted image frames 105*b* comprises a set of private information, e.g. information regarding the image, gender, age, nationality, and identity of the person. The neural network 601 trained with the images from the private blockchain network 106 is provided for generating the set of private information 105*c*.

A ML (Machine Learning) algorithm is used to normalize substantially all faces 105*b* of the training set accessible via the API 106*a*, for removing common features and projected as a weighted sum of the n-eigenvectors space of each feature of the faces. The data is classified based on the above-mentioned parameter such as gender, age, nationality.

After successfully importing the data 105*a* from the face recognition device 105' and/or from the unique feature recognition device 105" to the neural network 601, two Convolution Neural Network (CNN) models are built with the given data 105*a* and with the given parameters 105*b* age, nationality, and the gender. In an example, the images of the faces 105*b* are used as training data for neural network 601.

The input weight vector data 105*a*, e.g., the weight vector data of the face and the vector of the unique features, is/are compared and/or matched with all the weight vectors of the images 105*b* in the training set. In case the distance between the two vectors for face and unique features are above a predefined threshold for matched values, the images are outliers and do not match with the person that is needed to be identified. Comparing and/or matching the victim dataset 103 with a pre-definable probability and/or threshold may allow to set an accuracy level for the acceptable set of private information out of the plurality of private information, e.g. by weight vectors and/or distances. The lower the distance, the higher the accuracy and/or the probability of the match.

Once the smallest distance and/or the highest accuracy of the image under recognition 105*a* with the dataset 105*b* has been identified, the system 100 retrieves through the RESTAPI interface 106*a* the URLs from these images belonging to the selected set of private information 105*c*. The identity recognition device 107 forwards the at least one set of private information 105*c* and/or the list of matched images 105*c* to the identity processing device 108 where the at least one set of private information 105*c* is stored temporarily to the system's database, e.g. the victim identification database 104.

The RESTAPI interface 106*a* provides an interface to subscribe to and interact with the private blockchain network 106 of the governmental authorities. This private database 106 may keep private information of citizens such as photos and may be controlled by an executing official authority, e.g. by a police department, a social service and/or a passport insurance service. The blockchain network 106 has been selected to ensure that the system is immutable as the images and the owners of the images cannot be changed. The blockchain technology may ensure the integrity of the data by its decentralized architecture. Substantially only the government and governmental authorities have access to this private blockchain network 106.

Every encrypted image 105*b* stored in the private database 106 or the blockchain network 106 is related to a sequence of blocks that comprises information related to the original URL of the image, information about access permissions for an entity to each of the plurality of images 105*b* and identity information about the person to which the respective image is linked. Identity information for the person linked to the image may comprise sensitive information such as the name, surname, date of birth and social number of the person. This interface 106*a* offers to the system 100 an interaction point for submitting commands and for executing interactions with the blockchain network 106. The interaction with the interface 106*a* may be used for consuming and/or using services. Services that may be provided in the blockchain network 106 could be requesting an image, receiving a key index for an image, receiving a cipher text that is needed to decrypt an image as well as requesting the URLs of the images and/or of a set of private information.

The image frames are stored in the private database 106 as scrambled files and may be encrypted in order to protect the plurality of private information 105*b* from malicious usage. The image key and/or the key index of an image is used to prevent the unauthorized use of the images and the encryption handles the ordering of the frames. The way of accessing the blockchain may provide an additional level of security by encrypting the images of all the citizens related to the images. The cipher text is used to further ensure that the content of the image is not accessible and "readable" by unauthorized parties. This ensures that only authorized users and users who have the credentials add data to the blockchain. There are also additional policies that specify which image and for which purpose and/or for which timeslot, etc., someone has access. In addition, a transaction report can be generated which registers the user and the time for each transaction.

The output of the neural network 601 and of the identity recognition device 107 is at least one set of private information 105*c* and/or a list of matched images 105*c*. The at least one set of private information 105*c* comprises a list of people who match the image under recognition 105*a*, in particular a list of people who may have a similarity to the image of the victim.

This at least one set of private information 105*c* is forwarded or propagated to the identity processing device 108. The identity processing device 108 is adapted to send for every person and/or record entry in the at least one set of private information 105*c* a request to an activity database, e.g. to a social media network in order to retrieve publicly available information and/or photos of every person of the at least one set of private information 105*c*.

The identity processing device 108 can use a ML algorithm to process these publicly available photos, extract features and compare the extracted features with the images of the listed people of the at least one set of private information 105*c*. For this comparison different classifier algorithms may be used in the identity processing device 108. If additional information about a person is found in the public activity database 109 that may have a relevance to the incident and/or the location of the incident, the identity processing device 108 generates set of aggregated information with this additional activity information 109*a*.

Another example for activity information is trace data of a mobile network and/or login data to WiFi networks. Such information may help to provide location information of the person that is to be identified. Mobile network data may be retrieved from available telecommunication service providers. If those telecommunication service providers grant access to their databases, the information about the transmitting signal of the mobile phones of the people in the set of private information 105c may be retrieved. The transmitting signals and/or the radio signals may correlate with the area of incident. In this way, the probability for an identity of a person in the set of private information 105c may be increased and/or some sets of private information 105c may be excluded since they may be localized abroad and far away from the location of the incident. The additional activity information 109a may be aggregated with the corresponding at least one set of private information 105c and for each still relevant set of private information 105c at least one set of aggregated information may be generated.

In other words, the responses of the requests to the activity database 109 and the classified data are aggregated to at least one set of aggregated information, wherein the at least one set of aggregated information comprises the at least one set of private information 105c and activity information 109a associated with the at least one set of private information.

The at least one set of aggregated information is forwarded to the identity of recognized person selecting subcomponent 108a of the identity processing device 108. The Identity of recognized person selecting sub-component 108a is adapted for selecting from the at least one set of aggregated information a particular set of aggregated information which best matches the victim dataset 103 and/or the converted victim data set 105a.

The Identity of recognized person selecting sub-component 108a receives the response from the activity database 109, e.g. from a call database and/or a lawful interception database of a telecommunication service provider or from a database of a social media network. The Identity of recognized person selecting sub-component 108a also receives the set of private information 105c and/or the list of matched images 105c from the classifier algorithms from the identity recognition device 107. The Identity of recognized person selecting sub-component 108a of the identity processing device 108 is adapted for generating for each set of the at least one set of private information 105c at least one set of aggregated information, e.g., a combination of the set of private information 105c with corresponding activity information 109a, in order to process at least one set of aggregated information and select the best match with the victim dataset 103 and/or with the converted victim dataset 105a as the particular set of aggregated information 105d.

The selected particular set of aggregated information 105d is the particular set of aggregated information 105d that corresponds to the identity of the person in need with the highest probability between all the available sets of aggregated information. It takes into account the best match of the victims' image with the images of the plurality of private information 105b in the citizens database 106 and the activity for the person belonging to the particular set of aggregated information, e.g. the last location where a mobile phone of that person may have been logged in a mobile network or the last location from where the person sent information to a social network.

Figure 7:
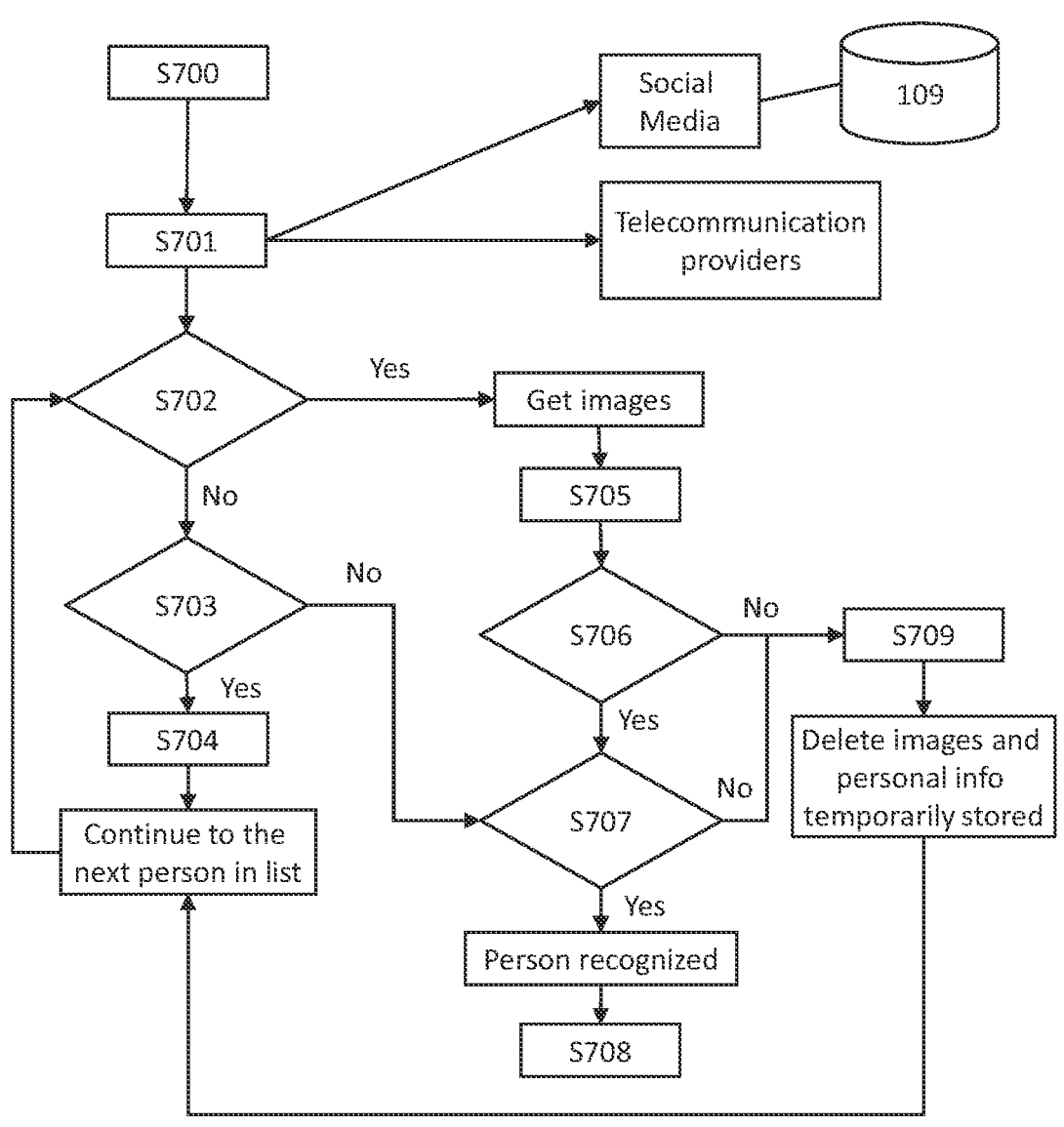
FIG. 7 shows a flowchart of a method for generating and selecting a particular set of aggregated information that best matches the victim dataset.

FIG. 7 shows a flowchart of a method for generating and selecting a particular set of aggregated information 105d that best matches the victim dataset 103.

The flowchart shows a process executed in the identity processing device 108, in particularly executed in the identity of recognized person selecting sub-component 108a. In an example, the identity of the person in need comprises the name, surname, date of birth and social number or social security number and other private data of the person in need.

Before the process starts in stage S700, a call is received from the user wherein the call comprises identification information gathered by the user 201, 202 and/or comprises position information of the user. A victim dataset 103 is generated from the identification information gathered by the user 201, 202, e.g. call number, IMSI (International Mobile Subscriber Identifier) and/or from the position information gathered by the user 201, 202.

The victim dataset 103 is stored in a victim identification database 104 and at least one set of private information 105c is retrieved from a private database 106 based on the victim dataset 103, wherein the at least one set of private information matches the victim dataset with a predefinable probability.

In stage S701, activity information 109a is collected for each set of the at least one set of private information 105c from a list of activity databases 109, wherein the activity information 109a is associated with the at least one set of private information 105c. In this way, location information and/or images for the listed people in the at least one set of private information 105c is retrieved. A listed person is a person who forms one sub-set of private information 105c in the at least one set of private information 105c.

A verification is made in stage S702 for each person in the list. The verification comprises a test whether the person has an image and information about his/her location and/or position stored in any activity database 109. For that purpose, a test is made whether the listed person from the set of private information 105c has a social media account and publicly accessible images uploaded to that account. In case the result of the algorithm leads to the output that the identified person may be the person on, for example, image A with a percentage of 85% and the person on image B with a percentage of 86%, this error needs to be eliminated. Additional images retrieved from social media could be used, e.g., from Instagram, Facebook, etc., to say with a higher accuracy, e.g. 94% that it is the person on image B.

As described in FIG. 6 the accuracy goes along with the distance between the two vectors for face and unique features and the lower the distance, the higher the accuracy and/or the probability of the match.

If no activity account 109 is available in stage S703, a test is made whether the at least one set of private information 105c comprises further listed persons and via stage S704 stage S702 is repeated with the next person of the at least one set of private information 105c without removing the actual person from that list.

If in stage S702 the test result is that the listed person from the set of private information 105c has a social media account and publicly accessible images uploaded to that account, the image is retrieved in stage S705 and compared with the images of the listed people, e.g., with all images retrieved from the private database 106 and which are now in the at least one set of private information 105c. For this comparison a probability is calculated that expresses the degree of similarity as to how the victim dataset matches the respective image of the at least one set of private information 105c.

If in stage S706 the probability of matching is detected as high, for example, if the accuracy is higher or equal to a predefined threshold, in stage S707 further information from the at least one set of private information 105c is considered and compared with the incident and/or with the victim. In an example, the position of the actual examined persons derived from the activity database 109 is compared to the location of the incident.

If the position of the at least one set of private information 105c matches the location of the incident in stage S708 the actual person of the at least one set of private information 105c is identified as the recognized person and/or the identity of the recognized person is provided as a particular set of aggregated information 105d.

In order to find the best match in addition to the threshold criteria a further criterion may be applied, in particular, if the accuracy threshold of two images is above the threshold but have a small difference between another. If, for example, the predefined threshold for a match is 91% and there are two images A and B, whereas A is 92% and B is 92.5%. In such cases an extra verification in addition to the threshold criteria may be needed. Such extra verification may be made by retrieving other information, e.g. further information for a user from different social media accounts.

Thus, not only a test is made whether the accuracy percentage is above a threshold. But also, a test is made whether the differences of all the matches above the threshold have a high enough difference to another. For that purpose, a difference threshold may be set up which needs to be exceeded before the selection of the best match is made.

By examining the matches and checking for the best match a situation may be prevented that the method would finish as soon as an acceptable accuracy of match is found in S706 and the location S707 matches. If the list contains an image with a higher accuracy and similar location, the method does not immediately stop but also the case with the higher accuracy is compared to all other matches above the threshold and only if the difference between all the matches is high enough, a decision is made for the best match. And, if necessary, further information from other resources is collected.

If the test for the matching probability in stage S706 is higher than or equal to a predefined accuracy level and/or the test for the location in stage S707 shows that the position of the person differs from the location of the incident, the actual person is removed from the list and/or from the at least one set of private information 105c, as shown in stage S709. The method continues with the next person in stage S704 and/or S702.

When in stage S708 a person is recognized and/or after all persons of the list 105c have been examined, the database 104 of the system 100 is updated. The update comprises the deletion of the temporary data of people 103 for who no match has been found and/or the deletion of at least one set of private information 105c if no match has been found at all. Also, the list with the matched scores is deleted in order to remove every private information from the system 100. In this way, data protection requirements may be met.

Stages S701 to S709 may be summarized as generating at least one set of aggregated information for every set of the at least one set of private information 105c, wherein the at least one set of aggregated information comprises the at least one set of private information 105c and activity information 109a associated with the at least one set of private information 105c. Furthermore, stages S701 to S709 comprise selecting from the at least one set of aggregated information a particular set of aggregated information 105d that best matches the victim dataset 103 and/or the converted victim dataset 105a.

Following the identity recognition in stages S701 to S709 of the person in need, the EHR is requested, and medical information is retrieved.

In other words, health record data is retrieved from a health record database 111 based on information from the particular best matching set of aggregated information 105d and the respective health record data and/or EHR is provided.

It should be noted that the term "comprising" does not exclude other elements or steps and the "a" or "an" does not exclude a plurality. Also, elements described in association with different embodiments may be combined.

It should also be noted that reference signs in the claims shall not be construed as limiting the scope of the claims.

It should be appreciated that different embodiments of the method, communication system, communication apparatus, and non-transitory computer readable medium can be developed to meet different sets of design criteria. For example, the particular type of network connection, server configuration or client configuration for a device for use in embodiments of the method can be adapted to account for different sets of design criteria. As yet another example, it is contemplated that a particular feature described, either individually or as part of an embodiment, can be combined with other individually described features, or parts of other embodiments. The elements and acts of the various embodiments described herein can therefore be combined to provide further embodiments. Thus, while certain exemplary embodiments of a telecommunication apparatus, telecommunication device, computer device, a network, a server, a communication system, and methods of making and using the same have been shown and described above, it is to be distinctly understood that the invention is not limited thereto but may be otherwise variously embodied and practiced within the scope of the following claims.

What is claimed is:

1. A method for providing health record data, comprising:

receiving data from a user, wherein the data comprises identification information gathered by the user and/or position information of the user, where receiving the data comprises authenticating and/or authorizing an originator of the data and/or a third party;

generating a victim dataset by a victim dataset generation device from the identification information gathered by the user and/or from the position information gathered by the user;

storing the victim dataset by the victim dataset generation device in a victim identification database;

retrieving, by an identity recognition device, from a private database at least one set of private information based on the victim dataset, wherein the at least one set of private information matches the victim dataset with a predefinable probability;

collecting, by an identity processing device, for each set of the at least one set of private information, activity information from a list of activity databases, wherein the activity information is associated with the at least one set of private information;

generating, by the identity processing device, for each set of the at least one set of private information at least one set of aggregated information, wherein the at least one set of aggregated information comprises a combination of the at least one set of private information and the collected activity information associated with the at least one set of private information;

selecting, by the identity processing device, from the at least one set of aggregated information a particular set of aggregated information that best matches the victim dataset;

retrieving, by a health record evaluation device, health record data from a health record database based on information from the particular set of aggregated information with the best match;

providing, by the health record evaluation device, the health record data; and generating and executing a smart contract based on the victim dataset and health record data, wherein the smart contract is a list of instructions which are carried out when loaded to a processor, wherein the private database, the activity database and/or the health record database is/are accessible via an Application Programming Interface (API).

2. The method of claim 1, further comprising monitoring the execution of the smart contract.

3. The method of claim 1, wherein the received information from the private database, the activity database and/or the health record database comprises a link to a location where the information is stored and/or the database is based on blockchain technology.

4. The method of claim 1, wherein the at least one set of private information comprises a list of matched images.

5. The method of claim 1, wherein the data is identified as an emergency call by a field in a data package of the emergency call.

6. The method of claim 1, wherein for matching the least one set of private information with the victim dataset a machine learning algorithm is used.

7. The method of claim 1, wherein generating a victim dataset comprises employing a face recognition process and/or a unique feature recognition process.

8. The method of claim 7, wherein the face recognition process and/or the unique feature recognition process comprise a correction process.

9. The method of claim 1, further comprising retrieving the identification information and/or the position information by a device close to the user.

10. A non-transitory computer-readable medium comprising program code, the code defining a method that is performed by a device that executes the code via a processor of the device, the method comprising:

receiving data from a user, wherein the data comprises identification information gathered by the user and/or position information of the user, and where receiving the data comprises authenticating and/or authorizing an originator of the data and/or a third party;

generating a victim dataset from the identification information gathered by the user and/or from the position information gathered by the user;

storing the victim dataset in a victim identification database;

retrieving, from a private database, at least one set of private information based on the victim dataset, wherein the at least one set of private information matches the victim dataset with a predefinable probability;

collecting, for each set of the at least one set of private information, activity information from a list of activity databases, wherein the activity information is associated with the at least one set of private information;

generating, for each set of the at least one set of private information, at least one set of aggregated information, wherein the at least one set of aggregated information comprises a combination of the at least one set of private information and the collected activity information associated with the at least one set of private information;

selecting, from the at least one set of aggregated information, a particular set of aggregated information that best matches the victim dataset;

retrieving health record data from a health record database based on information from the particular set of aggregated information with the best match;

providing the health record data; and generating and executing a smart contract based on the victim dataset and health record data, wherein the smart contract is a list of instructions which are carried out when loaded to a processor, wherein the private database, the activity database and/or the health record database is/are accessible via an Application Programming Interface (API).

11. A system for providing health record data comprising:

a receiving device;

a victim dataset generation device;

an identity recognition device;

an identity processing device; and a health record evaluation device;

wherein the receiving device is configured to receive data via a communication connection with a user device of a user, wherein the data comprises identification information gathered by a user and/or position information of the user, and where receiving the data comprises authenticating and/or authorizing an originator of the data and/or a third party;

wherein the victim dataset generation device is configured to generate a victim dataset from the identification information of the user and/or from the position information of the user; and store the victim dataset in a victim identification database;

wherein the identity recognition device is configured to retrieve from a private database at least one set of private information based on the victim dataset, wherein the at least one set of private information matches the victim dataset with a predefinable probability;

wherein the identity processing device is configured to collect, for each set of the at least one set of private information and activity information from a list of activity databases, wherein the activity information is associated with the at least one set of private information;

wherein the identity processing device is configured to generate for each set of the at least one set of private information at least one set of aggregated information, wherein the at least one set of aggregated information comprises a combination of the at least one set of private information and the collected activity information associated with the at least one set of private information; and wherein the identity processing device is configured to select from the at least one set of aggregated information a particular set of aggregated information which best matches the victim dataset;

wherein the health record evaluation device is configured to retrieve health record data from a health record database based on information from the particular set of aggregated information with the best match; and to provide the health record data; and wherein the system generates and executes a smart contract based on the victim dataset and health record data, wherein the smart contract is a list of instructions which are carried out when loaded to a processor, wherein the private database, the activity database and/or the health record database is/are accessible via an Application Programming Interface (API).

* * * * *